US00PP20413P2

(12) United States Plant Patent
van Nijnatten

(10) Patent No.: US PP20,413 P2
(45) Date of Patent: Oct. 13, 2009

(54) *CORYLUS* PLANT NAMED 'ANNY'S PURPLE DREAM'

(50) Latin Name: *Corylus avellana*
Varietal Denomination: Anny's Purple Dream

(76) Inventor: Andre F. van Nijnatten, Meirseweg 26, 4881 DJ, Zundert (NL)

( * ) Notice: Subject to any disclaimer, the term of this patent is extended or adjusted under 35 U.S.C. 154(b) by 0 days.

(21) Appl. No.: 12/231,451

(22) Filed: Sep. 3, 2008

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

UPOV-ROM GTITM, Plant Variety Database, 2009/02, GTI Jouve Retrieval Software, citation for 'Anny's Purple Dream'.*

* cited by examiner

*Primary Examiner*—Susan B McCormick Ewoldt
(74) *Attorney, Agent, or Firm*—Penny J. Aguirre

(57) ABSTRACT

A new cultivar of *Corylus* 'Anny's Purple Dream', characterized by its very compact plant habit, its slow growth rate, its large leaves, and its small sized leaves that are dark red in color.

2 Drawing Sheets

Botanical classification: *Corylus avellana*.
Variety denomination: 'Anny's Purple Dream'.

BACKGROUND OF THE INVENTION

The present invention relates to a new and distinct cultivar of *Corylus avellana*, and will be referred to hereafter by its cultivar name, 'Anny's Purple Dream'. 'Anny's Purple Dream' is a new cultivar of perennial shrub for use as a landscape plant.

The new cultivar of *Corylus*, 'Anny's Purple Dream', was discovered by the inventor in July of 1999 in Zundert, The Netherlands as a naturally occurring whole plant mutation in the inventor's garden. The parent plants of 'Anny's Purple Dream' are unknown.

Asexual reproduction of the new cultivar was first accomplished by grafting by the inventor in Zundert, The Netherlands in August 2001. The characteristics of this cultivar have been determined to be stable and are reproduced true to type in successive generations.

SUMMARY OF THE INVENTION

The following traits have been repeatedly observed and represent the characteristics of the new cultivar as grown outdoors in a test plot for eight years in Zundert, The Netherlands. These attributes in combination distinguish 'Anny's Purple Dream' as a unique cultivar of *Corylus* that is unlike any other cultivars of *Corylus* known to the inventor.

1. 'Anny's Purple Dream' has a very compact plant habit.
2. 'Anny's Purple Dream' has a slow rate of growth.
3. 'Anny's Purple Dream' exhibits leaves that are small in size.
4. 'Anny's Purple Dream' exhibits leaves that are dark red in color.

'Anny's Purple Dream' can be compared to the cultivar 'Anny's Compact Red' (not patented). 'Anny's Purple Dream' differs from 'Anny's Compact Red' in having a more compact plant habit, a slower speed of growth, smaller leaves, and leaves that are darker red in color. 'Anny's Purple Dream' can also be compared to 'Red Majestic' (U.S. Plant Pat. No. 16,048), which is similar in having burgundy foliage and a compact habit. 'Red Majestic' differs primarily in having a outward spreading to weeping plant habit with twisted stems and in having larger leaves.

BRIEF DESCRIPTION OF THE DRAWING

The accompanying colored photographs illustrates the overall appearance and distinct characteristics of 3 year-old plants of the new *Corylus* as grown in a trial plot in Zundert, The Netherlands. The plants were grafted on a 90 cm standards.

The photograph is

Figure 1:
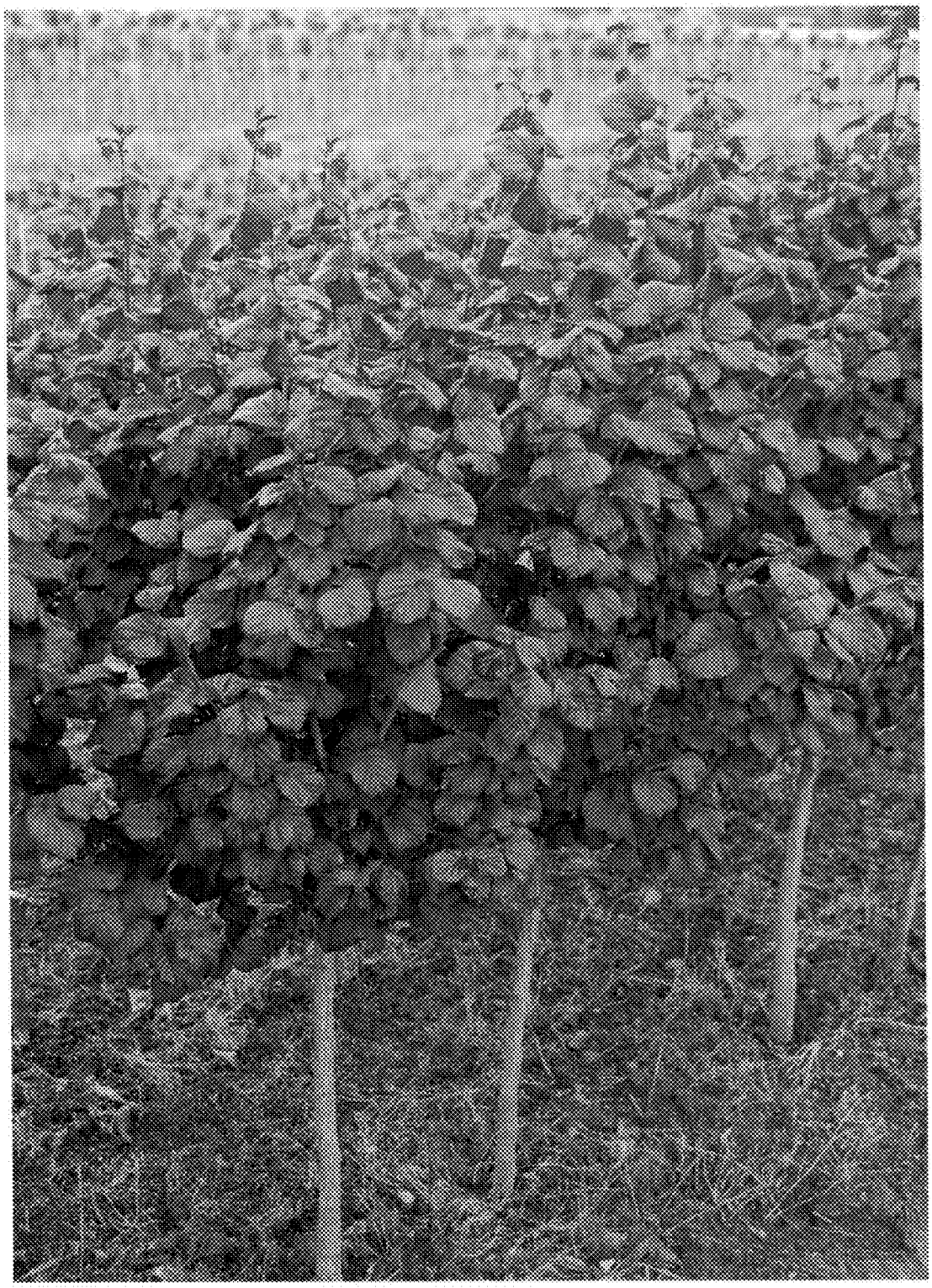
FIG. 1 illustrates its compact plant habit and the photograph in FIG. 2 provides a close-up view of the foliage of 'Anny's Purple Dream'.
Figure 2:
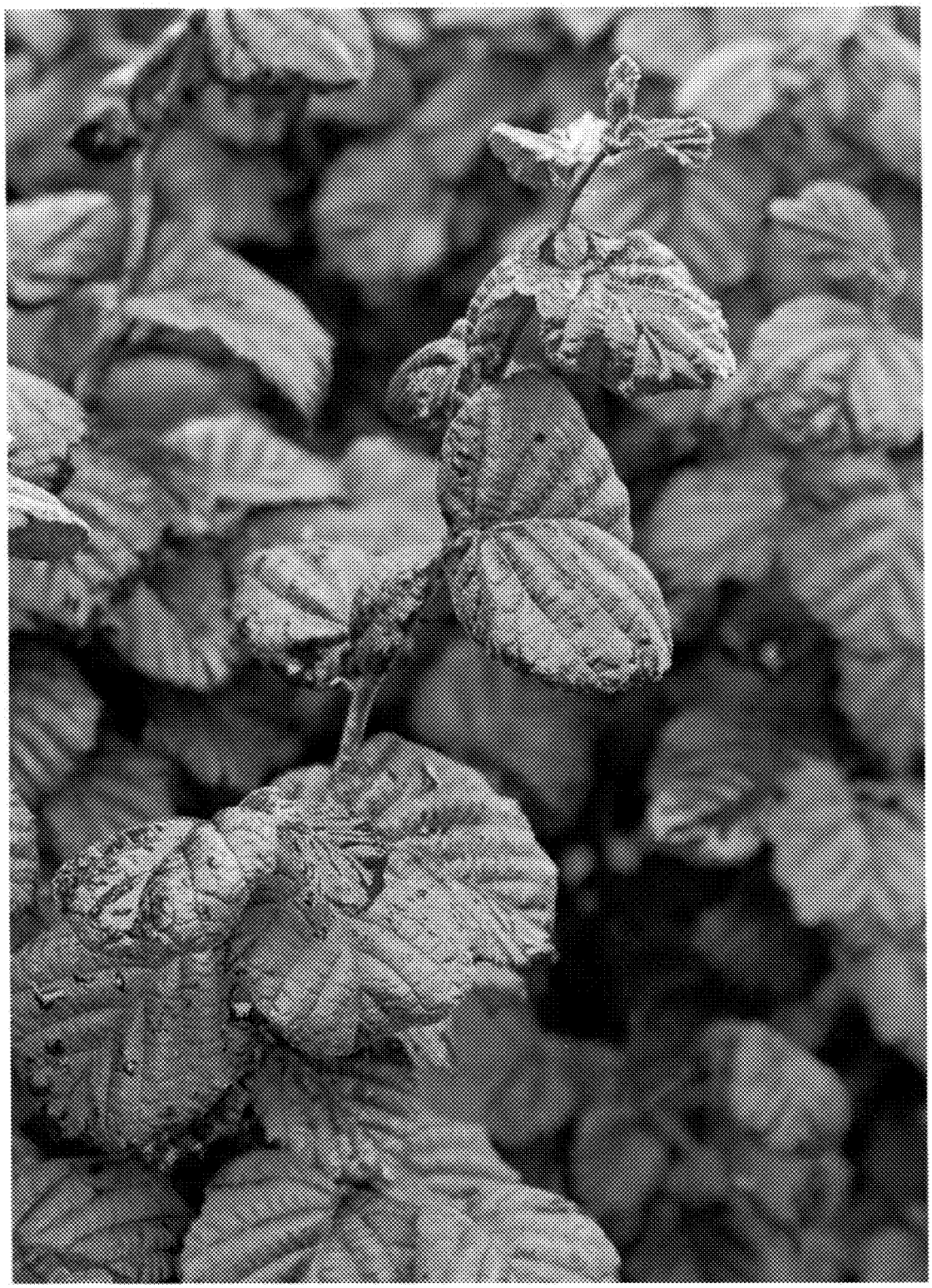

The colors in the photograph are as close as possible with the digital photography techniques available and the color values cited in the detailed botanical description most accurately describe the colors of the new *Corylus*.

DETAILED BOTANICAL DESCRIPTION

The following is a detailed description of 3 year-old plants of the new cultivar as grown outdoors in Zundert, The Netherlands in a trial bed and grafted onto standards 90 cm in length. The plants were grown with under average day temperatures of 12° to 27° C. and average night temperatures of 4° to 16° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Plant type.*—Deciduous, perennial shrub.

*Plant habit.*—Very compact, densely foliaged, broadly upright.

*Height and spread.*—Reaches about 80 cm in height and about 78 cm in width (in 3 years measured from graft).

*Cold hardiness.*—At least to U.S.D.A. Zone 6.

*Diseases and pests.*—No susceptibility or resistance to diseases or pests has been observed.

*Root description.*—Fine, freely branched..

*Propagation.*—Softwood cuttings and grafting, approximately 19 months from cuttings to produce a saleable plant.

*Growth rate.*—Slow.

Stem description:

*Shape.*—Rounded, strong.

*Stem color.*—New twigs N186C, mature bark 177A, bark N200B.

*Stem size.*—Lateral branches average 59 cm in length with young branches an average of 3 mm in diameter and older branches an average of 9 mm in diameter.

*Stem surface.*—Glossy, young stems are densely covered with short hairs; N186C in color.

*Branching.*—Freely branched; average of 21 lateral branches (3 years in age).

*Branch internode length.*—Average of 3.2 cm.

Foliage description:

*Leaf shape.*—Broadly ovate, convex.

*Leaf division.*—Simple.

*Leaf base.*—Cordate, touching to slightly overlapping.

*Leaf apex.*—Short apiculate.

*Leaf fragrance.*—None.

*Leaf venation.*—Pinnate, 148A in color on upper surface and 152A in color on lower surface.

*Leaf margins.*—Serrate.

*Leaf arrangement.*—Alternate.

*Leaf attachment.*—Petiolate.

*Leaf number.*—Average of 19 per lateral branch.

*Leaf surface.*—Upper surface; bullate, slightly glossy, covered with short hairs about N155B in color, lower surface; slightly glossy and covered with slightly longer hairs and about 157A in color.

*Leaf size.*—Average of 6.5 cm in length and 5.6 cm in width.

*Leaf internode length.*—Average of 2.5 cm.

*Leaf color.*—Newly expanded leaves upper surface; N186A to N186C, newly expanded leaves lower surface; N186C to 187A, mature leaves upper surface; 147A to N189A tinged with N186A, mature leaves lower surface; 147A.

*Petioles.*—Average of 1 cm in length and 1.5 mm in width, N186C in color, surface is glossy.

*Stipules.*—2 per petiole, leafy and drop when the leaf matures, ovate in shape, rounded apex, cuneate base, average of 6 mm in length and 2.5 mm in width, 146A to 146B, glabrous surface, serrated margins.

Flower description: Flower development has not been observed; under proper conditions, the new cultivar might produce small, insignificant flowers that are yellow in color.

It is claimed:

1. A new and distinct cultivar of *Corylus* plant named 'Anny's Purple Dream' as herein illustrated and described.

* * * * *